US011250977B2

(12) United States Patent
Iwamoto et al.

(10) Patent No.: US 11,250,977 B2
(45) Date of Patent: Feb. 15, 2022

(54) SUPERCONDUCTING MAGNET APPARATUS

(71) Applicant: Mitsubishi Electric Corporation, Chiyoda-ku (JP)

(72) Inventors: Naoki Iwamoto, Chiyoda-ku (JP); Masayoshi Oya, Chiyoda-ku (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 16 days.

(21) Appl. No.: 16/970,824

(22) PCT Filed: Nov. 8, 2018

(86) PCT No.: PCT/JP2018/041505
§ 371 (c)(1),
(2) Date: Aug. 18, 2020

(87) PCT Pub. No.: WO2019/198266
PCT Pub. Date: Oct. 17, 2019

(65) Prior Publication Data
US 2021/0057134 A1   Feb. 25, 2021

(30) Foreign Application Priority Data
Apr. 9, 2018   (JP) .............................. JP2018-074401

(51) Int. Cl.
*H01F 6/04* (2006.01)
*G01R 33/38* (2006.01)
*G01R 33/3815* (2006.01)

(52) U.S. Cl.
CPC ........... *H01F 6/04* (2013.01); *G01R 33/3804* (2013.01); *G01R 33/3815* (2013.01)

(58) Field of Classification Search
CPC .............................. H01F 6/04; G01R 33/3804
See application file for complete search history.

(56) References Cited

U.S. PATENT DOCUMENTS

| 2005/0252219 A1 | 11/2005 | Van Hasselt |
| 2011/0179809 A1 | 7/2011 | Zhang et al. |
| 2014/0329688 A1 | 11/2014 | Aoki et al. |

FOREIGN PATENT DOCUMENTS

| JP | 2005-530976 A | 10/2005 |
| JP | 2011-125686 A | 6/2011 |
| JP | 2013-118228 A | 6/2013 |
| WO | WO 2007-003499 A1 | 1/2007 |

OTHER PUBLICATIONS

International Search Report dated Dec. 25, 2018 in PCT/JP2018/041505 filed on Nov. 8, 2018, 2 pages.
Office Action dated Aug. 26, 2021, in corresponding Chinese patent Application No. 201880091589.7, 8 pages.

*Primary Examiner* — Ramon M Barrera
(74) *Attorney, Agent, or Firm* — Xsensus LLP

(57) ABSTRACT

A superconducting magnet apparatus includes a first superconducting coil centered around an axis extending in a direction intersecting with a vertical direction and a refrigerant circulation circuit through which refrigerant circulates. The refrigerant circulation circuit includes a first cooling pipe path in thermal contact with the first superconducting coil, an upper pipe path arranged above the first cooling pipe path, a lower pipe path arranged below the first cooling pipe path, and a connection pipe path that connects the upper pipe path and the lower pipe path to each other. The first cooling pipe path includes a first storage portion where refrigerant is stored.

13 Claims, 7 Drawing Sheets

SUPERCONDUCTING MAGNET APPARATUS

TECHNICAL FIELD

The present invention relates to a superconducting magnet apparatus and particularly to a superconducting magnet apparatus including a superconducting coil and a circuit through which refrigerant circulates, the circuit being thermally coupled to the superconducting coil.

BACKGROUND ART

Japanese Patent Laying-Open No. 2013-118228 discloses a superconducting magnet apparatus including a superconducting coil, a refrigerant circulation circuit (thermo-siphon) through which refrigerant for cooling the superconducting coil circulates, a protective resistor in thermal contact with the superconducting coil, and a high-boiling-point refrigerant supply section that supplies high-boiling-point refrigerant higher in boiling point than refrigerant into the protective resistor.

Furthermore, a magnetic resonance imaging (MRI) apparatus including a thermo-siphon superconducting magnet apparatus as above has been put into practical use.

CITATION LIST

Patent Literature

PTL 1: Japanese Patent Laying-Open No. 2013-118228

SUMMARY OF INVENTION

Technical Problem

In the thermo-siphon superconducting magnet apparatus as above, however, when a current is supplied to a superconducting coil to excite a superconducting magnet or when supply of the current is stopped to demagnetize the superconducting magnet, a current is fed to the protective resistor and transient heat generation occurs. Thus, the liquid level of refrigerant in the refrigerant circulation circuit becomes lower than a height of the superconducting coil, which may cause increase in temperature of the superconducting coil and loss of a superconducting state.

In order to suppress occurrence of such a problem, an amount of refrigerant (an amount of usage of refrigerant) sealed in the refrigerant circulation circuit should be increased.

A primary object of the present invention is to provide a superconducting magnet apparatus that achieves suppressed loss of a superconducting state during excitation or demagnetization while it achieves a smaller amount of usage of refrigerant than a conventional superconducting magnet apparatus.

Solution to Problem

A superconducting magnet apparatus according to the present invention includes a superconducting coil centered around an axis extending in a direction intersecting with a vertical direction, a refrigerant circulation circuit through which refrigerant circulates, and a cooling portion that cools refrigerant. The refrigerant circulation circuit includes a cooling pipe path in thermal contact with the superconducting coil, an upper pipe path connected to the cooling pipe path and arranged above the cooling pipe path, a lower pipe path connected to the cooling pipe path and arranged below the cooling pipe path, and a connection pipe path that connects the upper pipe path and the lower pipe path to each other. Refrigerant sequentially circulates through the cooling pipe path, the upper pipe path, the connection pipe path, and the lower pipe path. The cooling portion is provided to cool refrigerant in the upper pipe path. The cooling pipe path includes a storage portion where refrigerant is stored.

Advantageous Effects of Invention

According to the present invention, the first cooling pipe path thermally connected to the first superconducting coil includes the first storage portion where refrigerant is stored during excitation or demagnetization. Therefore, a superconducting magnet apparatus that achieves suppressed loss of a superconducting state during excitation or demagnetization while it achieves a smaller amount of usage of refrigerant than a conventional superconducting magnet apparatus and can be provided.

DESCRIPTION OF EMBODIMENTS

First Embodiment

<Construction of Superconducting Magnet Apparatus>

As shown in FIGS. 1 to 4, a superconducting magnet apparatus 100 includes a plurality of superconducting coils 1, a refrigerant circulation circuit 10 through which refrigerant circulates, and a cooling portion 20 that cools refrigerant.

Figure 1:
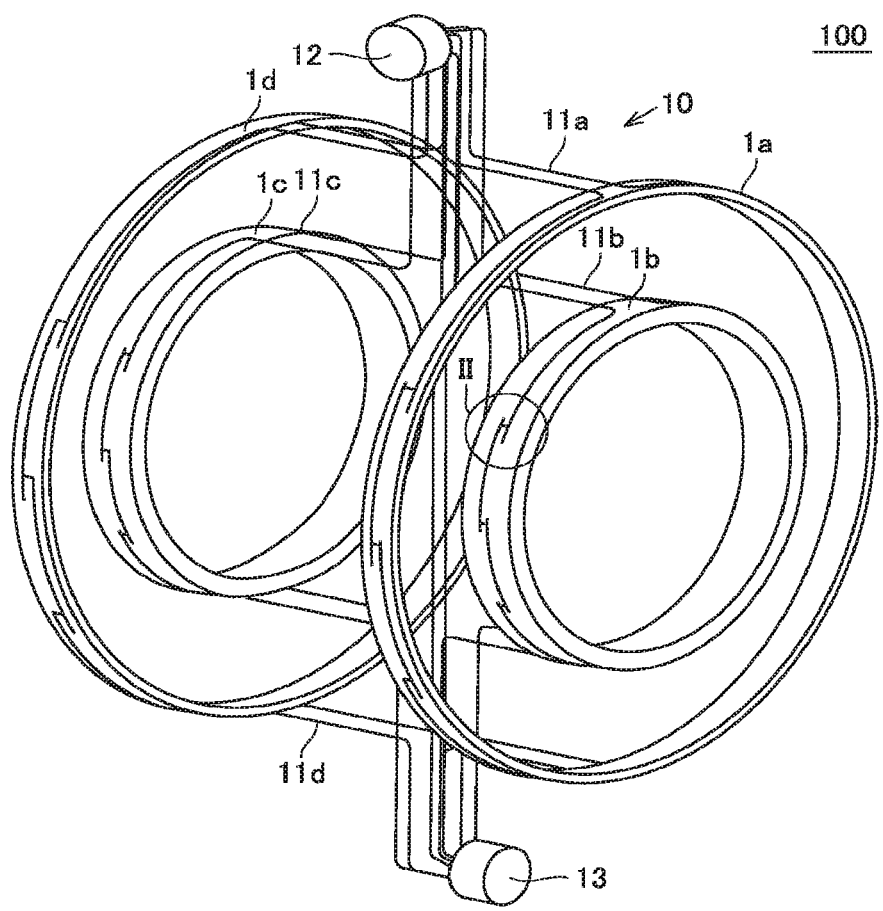
FIG. 1 is a perspective view showing a superconducting magnet apparatus according to a first embodiment.
Figure 2:
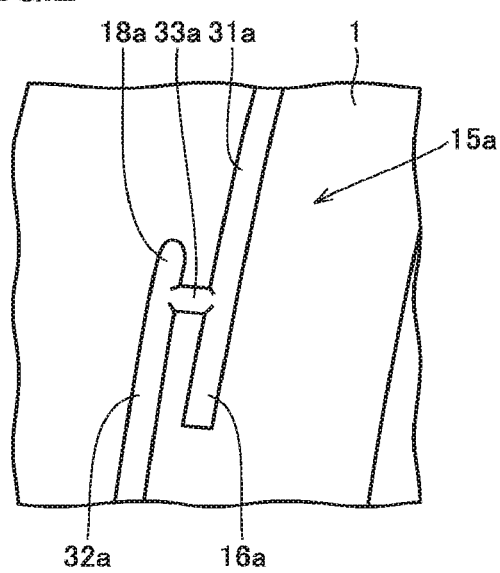
FIG. 2 is a partially enlarged view of a region II in FIG. 1.

Though the number of superconducting coils 1 is not particularly restricted, it is set, for example, to four as shown in FIG. 1. Each of the plurality of superconducting coils 1 extends in a circumferential direction around an axis extending in a direction intersecting with a vertical direction. The plurality of superconducting coils 1 include a first superconducting coil 1a, a second superconducting coil 1b, a third superconducting coil 1c, and a fourth superconducting coil 1d that are aligned in a direction of extension of the axis. The plurality of superconducting coils 1 are wound around a not-shown frame. A superconducting wire is employed as a material for the plurality of superconducting coils 1. The plurality of superconducting coils 1 may coaxially be arranged. The plurality of superconducting coils 1 may be arranged as being superimposed on one another in the direction of extension of the axis. First superconducting coil 1a is larger, for example, than second superconducting coil 1b in outer diameter. Second superconducting coil 1b is equal, for example, to third superconducting coil 1c in outer diameter. Fourth superconducting coil 1d is larger, for example, than third superconducting coil 1c in outer diameter.

Refrigerant circulation circuit 10 is filled with refrigerant. Refrigerant circulates through refrigerant circulation circuit 10 based on what is called a thermosiphon effect. For example, liquid helium is employed as refrigerant. Refrigerant circulation circuit 10 includes a plurality of cooling pipe paths 11a to 11d, an upper pipe path 12, a lower pipe path 13, and a connection pipe path 14. Refrigerant sequentially circulates through the plurality of cooling pipe paths 11a to 11d, upper pipe path 12, connection pipe path 14, and lower pipe path 13. A material for each pipe path that forms refrigerant circulation circuit 10 and a first storage portion 16a includes at least one selected from copper (Cu), aluminum (Al), and stainless steel (SUS). A pressure in refrigerant circulation circuit 10 is set, for example, to an atmospheric pressure or a pressure close to the atmospheric pressure.

The plurality of cooling pipe paths 11a to 11d are in thermal contact with the plurality of superconducting coils 1a to 1d. The plurality of cooling pipe paths 11a to 11d include a first cooling pipe path 11a in thermal contact with first superconducting coil 1a, a second cooling pipe path 11b in thermal contact with second superconducting coil 1b, a third cooling pipe path 11c in thermal contact with third superconducting coil 1c, and a fourth cooling pipe path 11d in thermal contact with fourth superconducting coil 1d. Each of the plurality of cooling pipe paths 11a to 11d includes a main pipe path through which refrigerant flows in the vertical direction and a storage portion provided in a portion intermediate in the main pipe path such that refrigerant remains therein also when a liquid level of refrigerant in the main pipe path lowers. First cooling pipe path 11a includes a first main pipe path 15a and first storage portion 16a branched from first main pipe path 15a. Second cooling pipe path 11b includes a second main pipe path 15b and a second storage portion 16b branched from second main pipe path 15b. Third cooling pipe path 11c includes a third main pipe path 15c and a third storage portion 16c branched from third main pipe path 15c. Fourth cooling pipe path 11d includes a fourth main pipe path 15d and a fourth storage portion 16d branched from fourth main pipe path 15d.

First cooling pipe path 11a further includes a lower storage portion 17a where refrigerant is stored, lower storage portion 17a being branched, for example, from first main pipe path 15a. Second cooling pipe path 11b further includes a lower storage portion 17b where refrigerant is stored, lower storage portion 17b being branched, for example, from second main pipe path 15b. Third cooling pipe path 11c further includes a lower storage portion 17c where refrigerant is stored, lower storage portion 17c being branched, for example, from third main pipe path 15c. Fourth cooling pipe path 11d further includes a lower storage portion 17d where refrigerant is stored, lower storage portion 17d being branched, for example, from fourth main pipe path 15d.

Upper pipe path 12 is arranged above the plurality of cooling pipe paths 11a to 11d. Upper pipe path 12 includes, for example, a tank where refrigerant in a liquid phase and refrigerant in a vapor phase are stored. In a portion of upper pipe path 12 where refrigerant in the vapor phase is stored, cooling portion 20 is arranged. Lower pipe path 13 is arranged below the plurality of cooling pipe paths 11a to 11d. Lower pipe path 13 includes, for example, a tank where refrigerant in the liquid phase is stored. In lower pipe path 13, for example, a not-shown protective resistor that prevents lowering in performance or burn damage of superconducting coil 1 on the occurrence of quench is arranged. The protective resistor is connected in parallel to the plurality of superconducting coils 1a to 1d.

Connection pipe path 14 connects upper pipe path 12 and lower pipe path 13 to each other. Connection pipe path 14 is connected to the plurality of cooling pipe paths 11a to 11d through upper pipe path 12 and connected to the plurality of cooling pipe paths 11a to 11d through lower pipe path 13.

Cooling portion 20 condenses refrigerant in the vapor phase to refrigerant in the liquid phase. Cooling portion 20 includes, for example, a low-temperature head 21 that is arranged in a portion of upper pipe path 12 where refrigerant in the vapor phase is stored and condenses refrigerant in the vapor phase. Refrigerant condensed in cooling portion 20 is allowed to flow into an upper portion of connection pipe path 14 in preference to each of cooling pipe paths 11a to 11d.

Superconducting magnet apparatus 100 may further include, for example, a not-shown spare cooling circuit through which helium gas circulates, in addition to refrigerant circulation circuit 10 and cooling portion 20. The spare cooling circuit is used in cooling superconducting coil 1 at a room temperature to a temperature equal to or lower than a critical temperature. A part of the spare cooling circuit also serves, for example, as a part of refrigerant circulation circuit 10. The spare cooling circuit cools superconducting coil 1 to a temperature equal to or lower than the critical temperature with three to five days being spent, for example, while it maintains a temperature of superconducting coil 1 within a predetermined temperature range such as a range not lower than a center value −20 K and not higher than the center value +20 K.

In superconducting magnet apparatus 100, for example, superconducting coils 1a to 1d are comparable to one another in construction, and for example, cooling pipe paths 11a to 11d are comparable to one another in construction. A construction of first superconducting coil 1a and first cooling pipe path 11a will representatively be described below.

<Construction of First Superconducting Coil and First Cooling Pipe Path>

First cooling pipe path 11a is blazed, for example, to an outer circumferential surface of first superconducting coil 1a. First cooling pipe path 11a may be blazed to an inner circumferential surface of first superconducting coil 1a or an outer circumferential surface of the frame. In any case described above, heat can conduct from one to the other of first cooling pipe path 11a and first superconducting coil 1a directly or through the frame. Therefore, first cooling pipe path 11a can be regarded as being in thermal contact with first superconducting coil 1a.

As shown in FIGS. 1 to 4, first cooling pipe path 11a includes an upper end located relatively above and a lower end located relatively below. First cooling pipe path 11a has the upper end connected to upper pipe path 12. First cooling pipe path 11a has the lower end connected to lower pipe path 13.

As shown in FIGS. 1 to 5, first cooling pipe path 11a includes first main pipe path 15a and first storage portion 16a branched from first main pipe path 15a. First main pipe path 15a connects upper pipe path 12 and lower pipe path 13 to each other. Though first main pipe path 15a may be in any construction, it includes, for example, a first pipe portion 31a and a second pipe portion 32a extending along the circumferential direction and a third pipe portion 33a extending along the axis. Second pipe portion 32a extends downward from a position above a lower end of first pipe portion 31a. First storage portion 16a is made up by a pipe branched downward from a portion intermediate in first main pipe path 15a and including a lower end along the outer circumferential surface of first superconducting coil 1a. Typically, the lower end of first storage portion 16a is located at a position higher than the lowermost position of first superconducting coil 1a and hence higher than lower pipe path 13.

As shown in FIGS. 1 to 5, first pipe portion 31a and second pipe portion 32a form an arc shape of which central angle with respect to the axis is smaller than 180 degrees. First pipe portion 31a is connected to upper pipe path 12. First pipe portion 31a and second pipe portion 32a are connected to each other through third pipe portion 33a. A portion of first pipe portion 31a connected to third pipe portion 33a is arranged above the lower end of first pipe portion 31a. A portion located below the portion of first pipe portion 31a connected to third pipe portion 33a makes up first storage portion 16a. First storage portion 16a has a bottom below a portion branched from first main pipe path 15a, that is, the portion of connection between first pipe portion 31a and third pipe portion 33a, and the bottom is made up by the lower end of first pipe portion 31a.

As shown in FIGS. 1 to 5, first main pipe path 15a is formed, for example, as a pipe path bent in an S shape or a Z shape and first storage portion 16a is branched from the bent portion. First main pipe path 15a is not limited to such a construction but may be formed, for example, as a linear pipe extending along one direction. In this case, first storage portion 16a may be formed, for example, as a pipe that is branched from a portion intermediate in first main pipe path 15a and bent downward.

As shown in FIGS. 1 and 3 to 5, first cooling pipe path 11a further includes lower storage portion 17a branched, for example, from first main pipe path 15a. First storage portion 16a and lower storage portion 17a are arranged at a distance from each other in the circumferential direction. Lower storage portion 17a is arranged below first storage portion 16a.

First main pipe path 15a further includes, for example, a fourth pipe portion 34a extending along the circumferential direction and a fifth pipe portion 35a extending along the axis. Fourth pipe portion 34a is arranged, for example, at a distance from first pipe portion 31a in the circumferential direction. Fourth pipe portion 34a is connected to lower pipe path 13. Fifth pipe portion 35a is arranged, for example, at a distance from third pipe portion 33a in the circumferential direction. A portion of second pipe portion 32a connected to fifth pipe portion 35a is arranged above the lower end of second pipe portion 32a. A portion located below the portion of second pipe portion 32a connected to fifth pipe portion 35a makes up lower storage portion 17a.

As shown in FIGS. 1 to 4, a portion of connection between second pipe portion 32a and third pipe portion 33a is arranged, for example, below the upper end of second pipe portion 32. From a different point of view, second pipe portion 32a includes, for example, a protruding portion 18a that protrudes above the portion of connection to third pipe portion 33a. Protruding portion 18a is smaller in volume than first storage portion 16a. A portion of connection between fourth pipe portion 34a and fifth pipe portion 35a is arranged, for example, below the upper end of fourth pipe portion 34a. From a different point of view, fourth pipe portion 34a includes, for example, a protruding portion protruding above the portion of connection to fifth pipe portion 35a.

As described above, first cooling pipe path 11a is entirely in thermal contact with first superconducting coil 1a. Namely, first pipe portion 31a, second pipe portion 32a, third pipe portion 33a, fourth pipe portion 34a, fifth pipe portion 35a, first storage portion 16a, and lower storage portion 17a are in thermal contact with first superconducting coil 1a.

Figure 3:
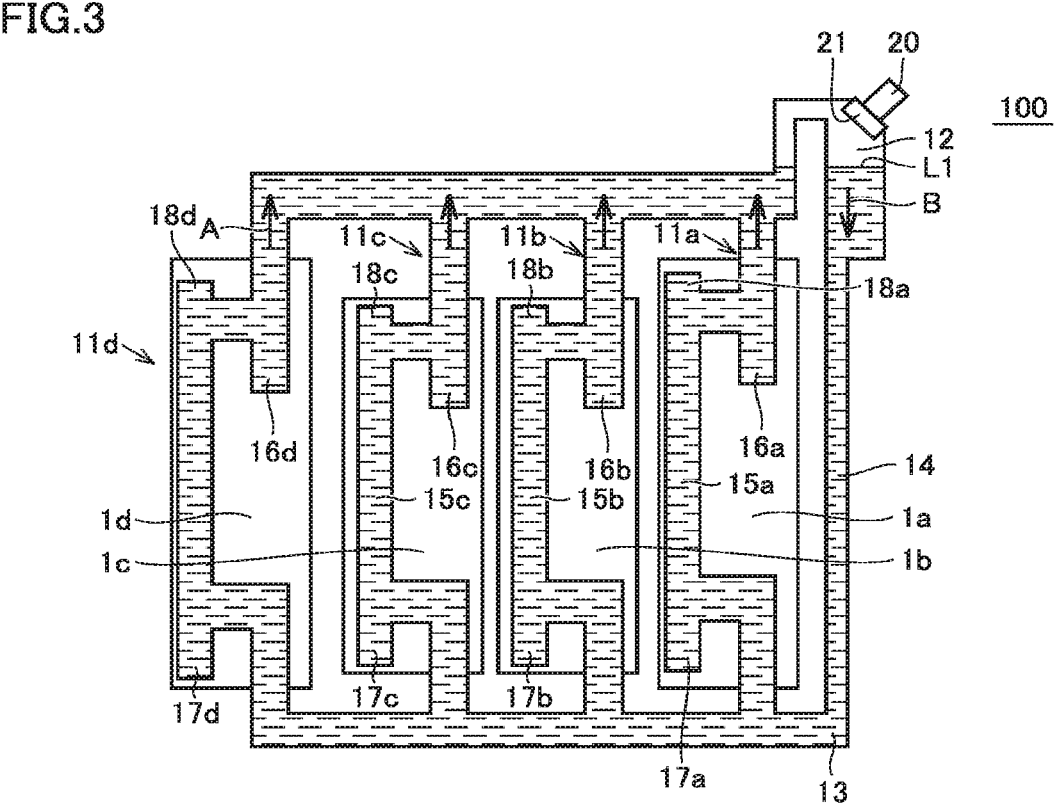
FIG. 3 is a diagram showing a liquid level of refrigerant in a refrigerant circulation circuit while the superconducting magnet apparatus according to the first embodiment is normally operating.

As shown in FIG. 3, refrigerant circulation circuit 10 is filled with refrigerant such that a liquid level L1 of refrigerant is located in upper pipe path 12 when superconducting magnet apparatus 100 is normally operating. The normal operation of superconducting magnet apparatus 100 refers to an operation in which the entire superconducting coil 1 is in a superconducting state and no local normal transition occurs in superconducting coil 1. During the normal operation, a region located below liquid level L1 in refrigerant circulation circuit 10 is filled with refrigerant in the liquid phase. A region located above liquid level L1 alone in refrigerant circulation circuit 10 is filled with refrigerant in the vapor phase. When heat intrudes into superconducting coil 1 from the outside of superconducting magnet apparatus 100 during the normal operation, heat is consumed as the temperature of refrigerant is increased and refrigerant is evaporated by heat. Refrigerant in the vapor phase that has evaporated in cooling pipe paths 11a to 11d moves in a direction shown with an arrow A, is emitted from cooling pipe paths 11a to 11d, and is stored in upper pipe path 12. Refrigerant in the vapor phase stored in upper pipe path 12 is cooled by low-temperature head 21 of cooling portion 20 and condensed to refrigerant in the liquid phase. Refrigerant in the liquid phase moves in a direction shown with an arrow B in connection pipe path 14. Thus, refrigerant recirculates through refrigerant circulation circuit 10 owing to what is called a thermo-siphon effect.

With increase in quantity of heat that intrudes into superconducting coil 1, an amount of refrigerant in the vapor phase increases. Therefore, the liquid level of refrigerant in refrigerant circulation circuit 10 lowers. In particular, when a quantity of heat consumed for evaporation of refrigerant is larger than cooling capability of cooling portion 20, the liquid level of refrigerant becomes lower than liquid level L1 shown in FIG. 3. During excitation or demagnetization of a superconducting magnet as well, a current is fed to the protective resistor and transient heat generation occurs. In this case, refrigerant in lower pipe path 13 where the protective resistor is arranged in refrigerant circulation circuit 10 is evaporated by heat from the protective resistor. Since a quantity of heat generation in the protective resistor during excitation or demagnetization is generally larger than cooling capability of cooling portion 20, the liquid level of refrigerant becomes lower than liquid level L1 shown in FIG. 3. Thus, refrigerant circulation circuit 10 maintains the temperature of superconducting coil 1 at a temperature equal to or lower than the critical temperature (for example, 6.0 K or lower) by changing a phase of refrigerant when heat intrudes into superconducting coil 1 or heat is generated in the protective resistor.

Figure 4:
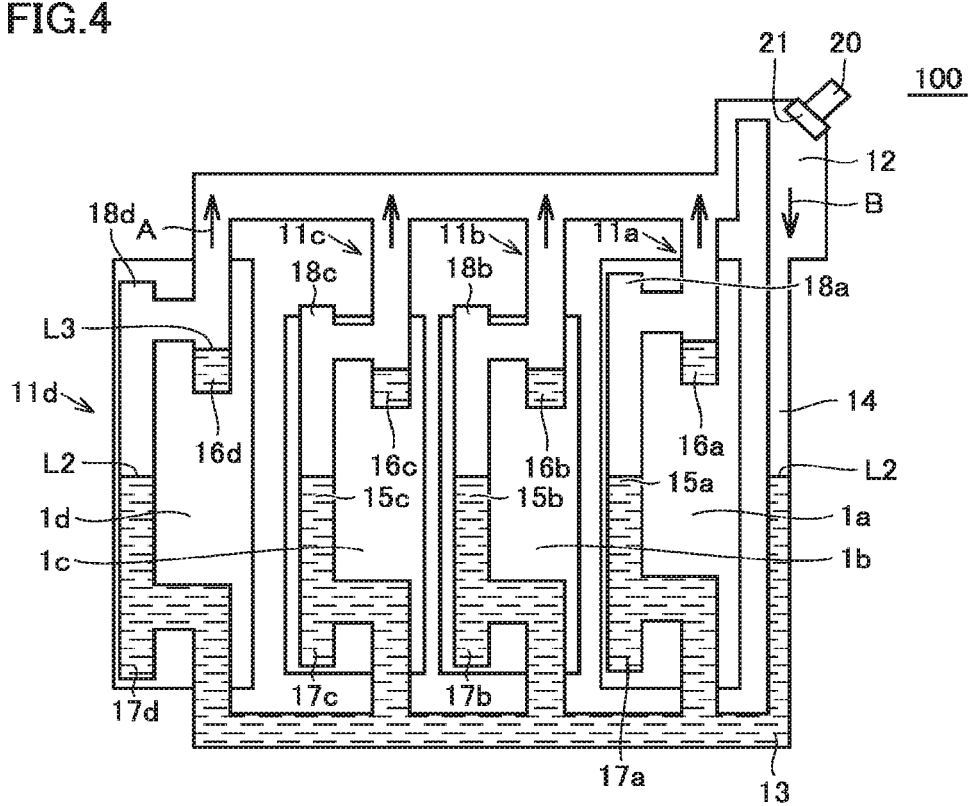
FIG. 4 is a diagram showing a liquid level of refrigerant in the refrigerant circulation circuit when a superconducting coil of the superconducting magnet apparatus according to the first embodiment is excited or demagnetized.
Figure 5:
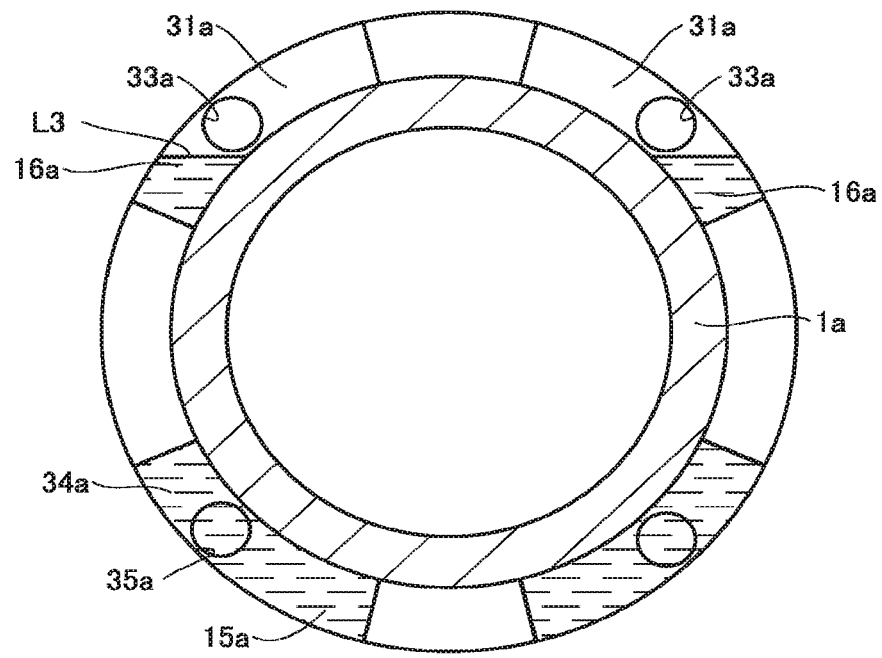
FIG. 5 is a cross-sectional view of the refrigerant circulation circuit shown in FIG. 4.

In superconducting magnet apparatus 100, a state shown in FIG. 4 can be realized. The state shown in FIG. 4 is realized, for example, when heat intrudes into portions of the plurality of superconducting coils 1 distant from a portion in thermal contact with storage portions 16a to 16d from the outside and a quantity of heat intrusion is larger than the quantity during the normal operation shown in FIG. 3. Alternatively, the state shown in FIG. 4 can be realized when the protective resistor transiently generates heat as described above. In the state shown in FIG. 4, the liquid level of refrigerant is located within main pipe paths 15a to 15d, storage portions 16a to 16d, and connection pipe path 14. A liquid level L2 of refrigerant located within main pipe paths 15a to 15d and connection pipe path 14 is located below a liquid level L3 of refrigerant located within storage portions 16a to 16d. In this case, refrigerant in the liquid phase stored in storage portions 16a to 16d cools portions of the plurality of superconducting coils 1a to 1d in thermal contact with storage portions 16a to 16d, and in some cases, refrigerant is evaporated. Refrigerant in the vapor phase that is evaporated in storage portions 16a to 16d is condensed in upper pipe path 12 similarly to refrigerant in the vapor phase that is evaporated in first main pipe path 15a or lower pipe path 13 and circulates through refrigerant circulation circuit 10. Thus, refrigerant in the liquid phase stored in storage portions 16a to 16d in FIG. 4 also contributes to heat transport by refrigerant circulation circuit 10.

<Function and Effect>

Superconducting magnet apparatus 100 includes the first superconducting coil centered around the axis extending in the direction intersecting with the vertical direction, the refrigerant circulation circuit through which refrigerant circulates, and the cooling portion that cools refrigerant. Refrigerant circulation circuit 10 includes first cooling pipe path 11a in thermal contact with first superconducting coil 1a, upper pipe path 12 arranged above first cooling pipe path 11a, lower pipe path 13 arranged below first cooling pipe path 11a, and connection pipe path 14 that connects upper pipe path 12 and lower pipe path 13 to each other. Refrigerant sequentially circulates through first cooling pipe path 11a, upper pipe path 12, connection pipe path 14, and lower pipe path 13.

Cooling portion 20 is provided to cool refrigerant in upper pipe path 12. First cooling pipe path 11a includes first main pipe path 15a that connects upper pipe path 12 and lower pipe path 13 to each other and first storage portion 16a where refrigerant is stored, first storage portion 16a being branched from first main pipe path 15a.

Superconducting magnet apparatus 100 can be in a state shown in FIG. 4. Refrigerant circulation circuit 10 can quickly remove heat that has intruded into the portion of first superconducting coil 1a located above liquid level L2 of refrigerant owing to refrigerant in the liquid phase stored in first storage portion 16a, also in a state that an amount of refrigerant in the vapor phase is relatively large as shown in FIG. 4. Namely, superconducting magnet apparatus 100 can achieve suppressed occurrence of dry-out due to shortage of refrigerant in the liquid phase and can prevent occurrence of quench more effectively than the conventional superconducting magnet apparatus without first storage portion 16a.

In order to prevent occurrence of quench in the conventional superconducting magnet apparatus without first storage portion 16a, an amount of refrigerant with which the refrigerant circulation circuit is filled should be increased to maintain the liquid level of refrigerant at a position relatively high in the cooling pipe path also in the state that the amount of refrigerant in the vapor phase is relatively large. In contrast, in superconducting magnet apparatus 100, the state shown in FIG. 4 where liquid level L3 of refrigerant in first storage portion 16a is located above liquid level L2 of refrigerant in first main pipe path 15a can be realized. Therefore, superconducting magnet apparatus 100 can prevent occurrence of quench more effectively than the conventional superconducting magnet apparatus without first storage portion 16a, while it achieves reduction in amount of refrigerant.

Furthermore, in superconducting magnet apparatus 100, second superconducting coil 1b, third superconducting coil 1c, and fourth superconducting coil 1d are similar in construction to first superconducting coil 1a, and second cooling pipe path 11b, third cooling pipe path 11c, and fourth cooling pipe path 11d are similar in construction to first cooling pipe path 11a. Therefore, superconducting magnet apparatus 100 provided with first storage portion 16a, second storage portion 16c, third storage portion 16c, and fourth storage portion 16d can more effectively prevent occurrence of quench than the conventional superconducting magnet apparatus without these components.

First cooling pipe path 11a further includes lower storage portion 17a where refrigerant is stored, lower storage portion 17a being branched from first main pipe path 15a in a portion below first storage portion 16a. First storage portion 16a and lower storage portion 17a are arranged at a distance from each other in the circumferential direction. Second cooling pipe path 11b further includes lower storage portion 17b where refrigerant is stored, lower storage portion 17b being branched from second main pipe path 15b in a portion below second storage portion 16b. Third cooling pipe path 11c further includes lower storage portion 17c where refrigerant is stored, lower storage portion 17c being branched from third main pipe path 15c in a portion below third storage portion 16c. Fourth cooling pipe path 11d further includes lower storage portion 17d where refrigerant is stored, lower storage portion 17d being branched from fourth main pipe path 15d in a portion below fourth storage portion 16d. Then, for example, a state that the liquid level of refrigerant in main pipe path 15a is located below lower storage portion 17a and refrigerant in the liquid phase is stored in first storage portion 16a and lower storage portion 17a can be realized. Therefore, superconducting magnet apparatus 100 can prevent occurrence of quench more effectively than the conventional superconducting magnet apparatus without storage portions 16a to 16d and lower storage portions 17a to 17d, while it achieves reduction in amount of refrigerant.

Figure 6:
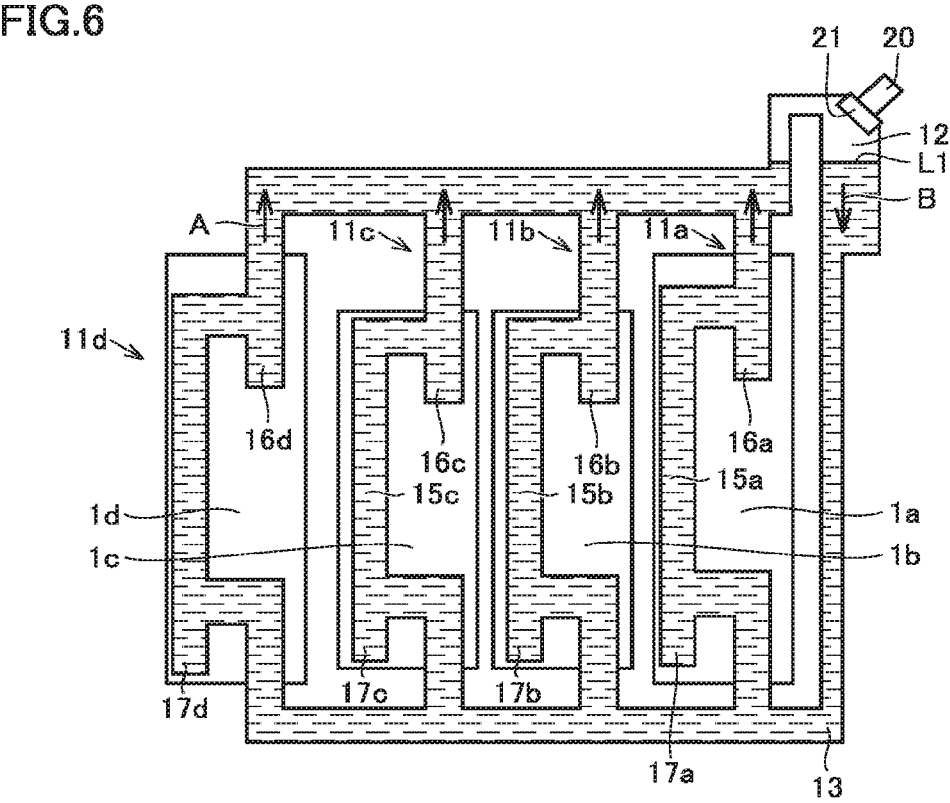
FIG. 6 is a diagram showing a superconducting magnet apparatus according to a second embodiment.

The plurality of cooling pipe paths 11a to 11d include protruding portions 18a to 18d, respectively. Such cooling pipe paths can relatively easily be formed by connecting a plurality of pipe portions by welding or the like. Such cooling pipe paths are lower in possibility of fracture or the like due to thermal stress than in an example where a cooling pipe path is formed by bending a linear pipe path. As shown in FIG. 6, the plurality of cooling pipe paths 11a to 11d do not have to include protruding portions 18a to 18d shown in FIG. 3.

Second Embodiment

Figure 7:
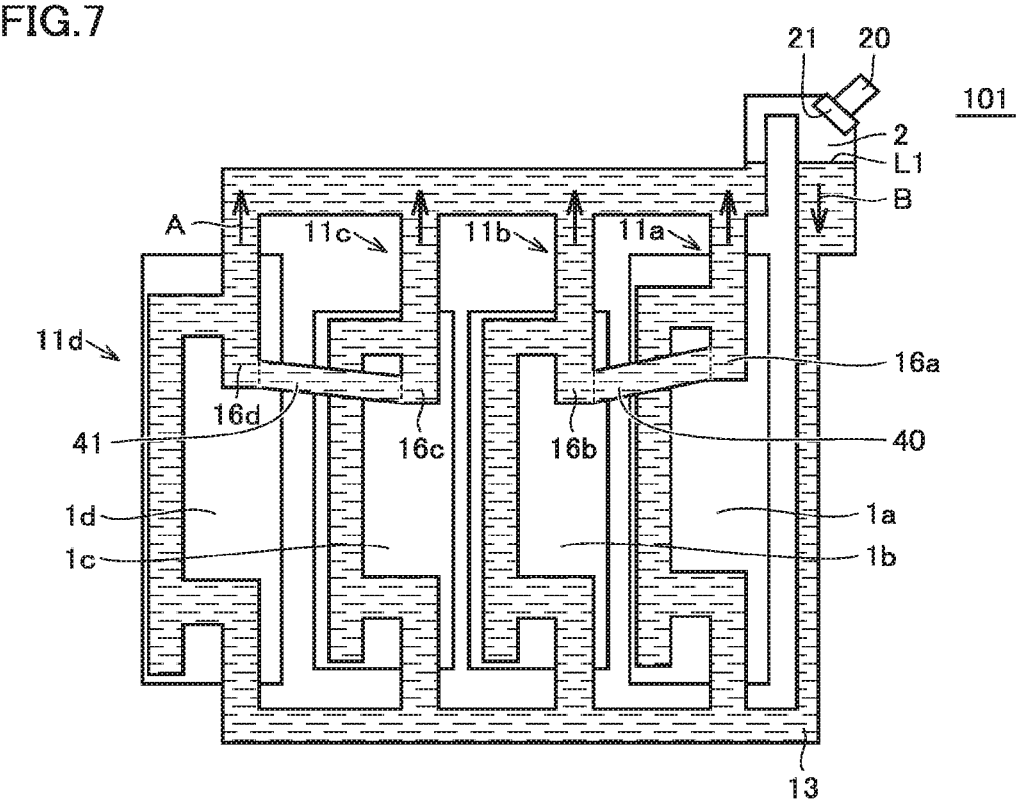
FIG. 7 is a diagram showing a liquid level of refrigerant in the refrigerant circulation circuit while the superconducting magnet apparatus according to the second embodiment is normally operating.
Figure 8:
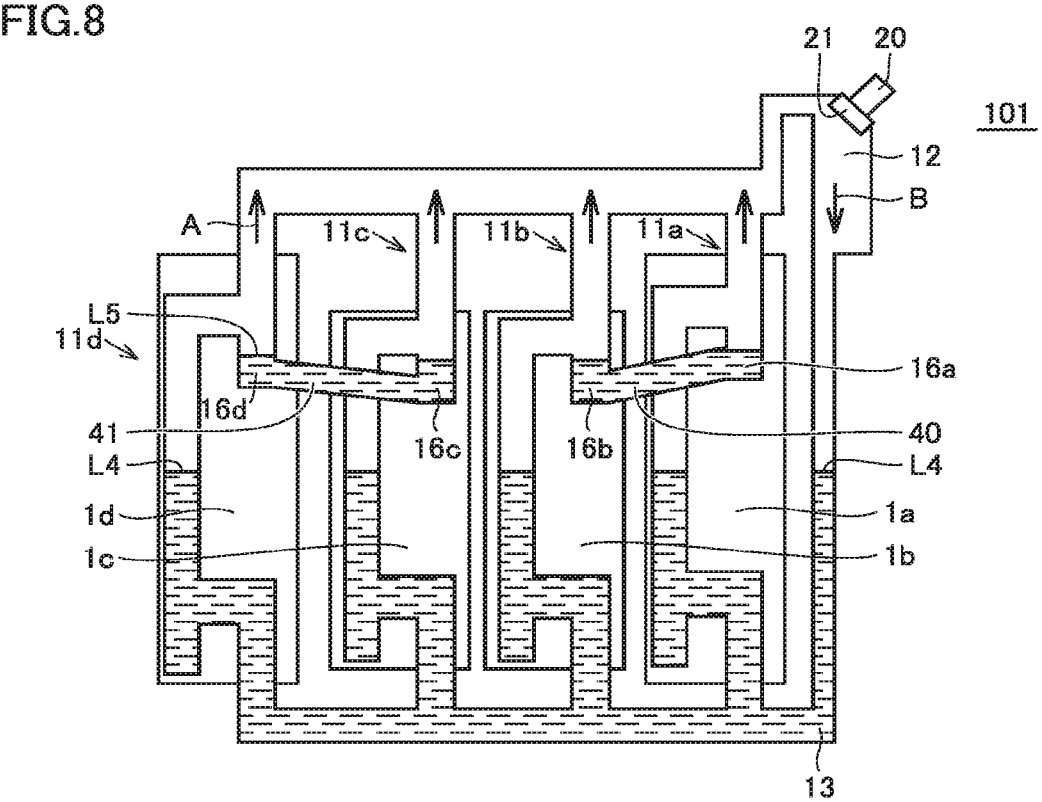
FIG. 8 is a diagram showing a liquid level of refrigerant in the refrigerant circulation circuit when a superconducting coil of the superconducting magnet apparatus according to the second embodiment is excited or demagnetized.

Though a superconducting magnet apparatus 101 according to a second embodiment is basically similar in construction to superconducting magnet apparatus 100 according to the first embodiment as shown in FIGS. 7 and 8, it is different in that refrigerant circulation circuit 10 further includes a communication pipe path 40 as a first communication pipe path that allows communication between first storage portion 16a of first cooling pipe path 11a and second storage portion 16b of second cooling pipe path 11b.

Refrigerant circulation circuit 10 further includes, for example, a communication pipe path 41 as the first communication pipe path that allows communication between third storage portion 16c of third cooling pipe path 11c and fourth storage portion 16d of fourth cooling pipe path 11d.

Communication pipe path 40 allows communication, for example, between a lower end of first storage portion 16a and a lower end of second storage portion 16b. Communication pipe path 41 allows communication, for example, between a lower end of third storage portion 16c and a lower end of fourth storage portion 16d. Communication pipe path 40 and communication pipe path 41 extend, for example, along a direction inclined with respect to a horizontal direction. A lower end of a portion of connection between communication pipe path 40 and first storage portion 16a is arranged, for example, between a lower end and an upper end of a portion of connection between communication pipe path 40 and second storage portion 16b. Second storage portion 16b is arranged, for example, below first storage portion 16a. Communication pipe path 40 is arranged, for example, at a longer distance from first superconducting coil 1a than first main pipe path 15a and first storage portion 16a. Communication pipe path 41 is arranged, for example, at a longer distance from third superconducting coil 1c than third main pipe path 15c and third storage portion 16c. A lower end of a portion of connection between communication pipe path 41 and fourth storage portion 16d is arranged, for example, between a lower end and an upper end of a portion of connection between communication pipe path 41 and third storage portion 16c.

Since superconducting magnet apparatus 101 is basically similar in construction to superconducting magnet apparatus 100, an effect similar to that of superconducting magnet apparatus 100 can be achieved.

Furthermore, in superconducting magnet apparatus 101, for example, when heat intrudes into first superconducting coil 1a in quantity larger than heat into second superconducting coil 1b and all of refrigerant in the liquid phase stored in first storage portion 16a is evaporated, some of refrigerant in the liquid phase stored in second storage portion 16b is supplied into first storage portion 16a through communication pipe path 40. Refrigerant in the liquid phase is moved through communication pipe path 40 by gravity. Therefore, in superconducting magnet apparatus 101, occurrence of quench is prevented more effectively than in superconducting magnet apparatus 100 also when a quantity of heat intrusion is varied among the plurality of superconducting coils 1a to 1d.

As shown in FIG. 8, when second storage portion 16b is arranged below first storage portion 16a, a larger amount of refrigerant in the liquid phase can be stored in second storage portion 16b than in first storage portion 16a. Therefore, for example, when second superconducting coil 1b is more susceptible to heat intrusion from the outside than first superconducting coil 1a, occurrence of quench in second superconducting coil 1b can effectively be prevented.

Communication pipe path 40 and communication pipe path 41 may extend along the horizontal direction.

Third Embodiment

Figure 9:
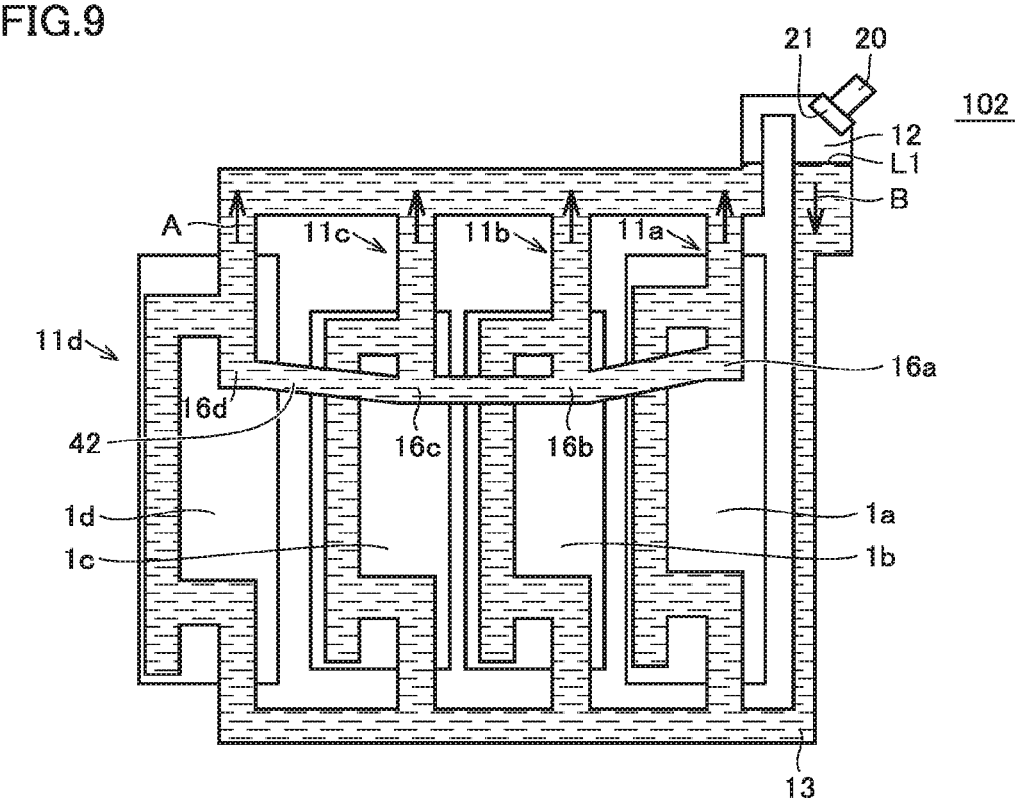
FIG. 9 is a diagram showing a liquid level of refrigerant in the refrigerant circulation circuit while a superconducting magnet apparatus according to a third embodiment is normally operating.
Figure 10:
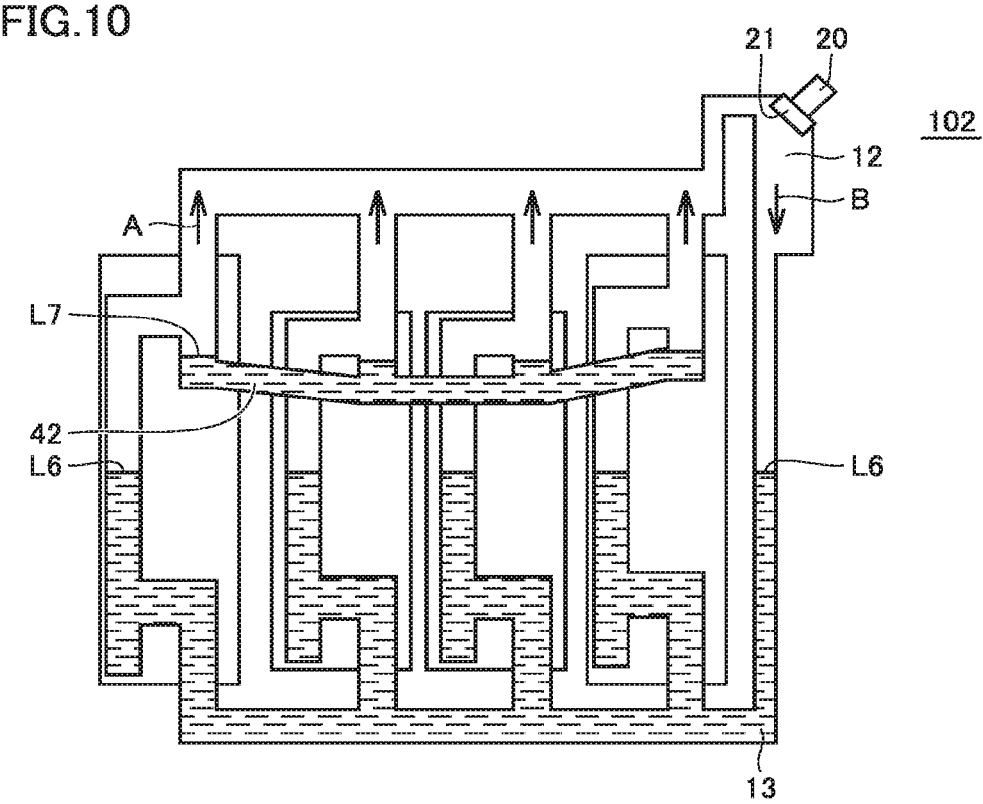
FIG. 10 is a diagram showing a liquid level of refrigerant in the refrigerant circulation circuit when a superconducting coil of the superconducting magnet apparatus according to the third embodiment is excited or demagnetized.

Though a superconducting magnet apparatus 102 according to a third embodiment is basically similar in construction to superconducting magnet apparatus 100 according to the first embodiment as shown in FIGS. 9 and 10, it is different in that refrigerant circulation circuit 10 further includes a communication pipe path 42 as the first communication pipe path that allows communication among first storage portion 16a, second storage portion 16b, third storage portion 16c, and fourth storage portion 16d.

Cooling pipe path 42 allows communication among first storage portion 16a of first cooling pipe path 11a, second storage portion 16b of second cooling pipe path 11b, third storage portion 16c of third cooling pipe path 11c, and fourth storage portion 16d of fourth cooling pipe path 11d. A portion that allows communication between first storage portion 16a and second storage portion 16b and a portion that allows communication between third storage portion 16c and fourth storage portion 16d in communication pipe path 42 extend, for example, along a direction inclined with respect to the horizontal direction. A portion that allows communication between second storage portion 16b and third storage portion 16c in communication pipe path 42 extends, for example, along the horizontal direction. A lower end of a portion of connection between communication pipe path 42 and first storage portion 16a is arranged, for example, between a lower end and an upper end of a portion of connection between communication pipe path 42 and second storage portion 16b. A lower end of a portion of connection between communication pipe path 42 and fourth storage portion 16d is arranged, for example, between a lower end and an upper end of a portion of connection between communication pipe path 42 and third storage portion 16c.

Communication pipe path 42 is arranged, for example, at a longer distance from first superconducting coil 1a, second superconducting coil 1b, and third superconducting coil 1c than first main pipe path 15a, second main pipe path 15b, third main pipe path 15c, first storage portion 16a, second storage portion 16b, and third storage portion 16c.

Since superconducting magnet apparatus 102 is basically similar in construction to superconducting magnet apparatus 100, an effect similar to that of superconducting magnet apparatus 100 can be achieved.

Furthermore, in superconducting magnet apparatus 102, for example, when heat intrudes into first superconducting coil 1a in quantity larger than heat into other superconducting coils 1b to 1d and all of refrigerant in the liquid phase stored in first storage portion 16a is evaporated, some of refrigerant in the liquid phase stored in second storage portion 16b, third storage portion 16c, and fourth storage portion 16d is supplied into first storage portion 16a through communication pipe path 42. Refrigerant in the liquid phase is moved through communication pipe path 42 by gravity. Therefore, in superconducting magnet apparatus 102, occurrence of quench is prevented more effectively than in superconducting magnet apparatus 100 also when a quantity of heat intrusion is varied among the plurality of superconducting coils 1a to 1d.

As shown in FIG. 10, when second storage portion 16b and third storage portion 16c are arranged below first storage portion 16a and fourth storage portion 16d, a larger amount of refrigerant in the liquid phase can be stored in second storage portion 16b and third storage portion 16c than in first storage portion 16a and fourth storage portion 16d. Therefore, for example, when second superconducting coil 1b and third superconducting coil 1c are more susceptible to heat intrusion from the outside than first superconducting coil 1a and fourth superconducting coil 1d, occurrence of quench in second superconducting coil 1b and third superconducting coil 1c can effectively be prevented.

Fourth Embodiment

Figure 11:
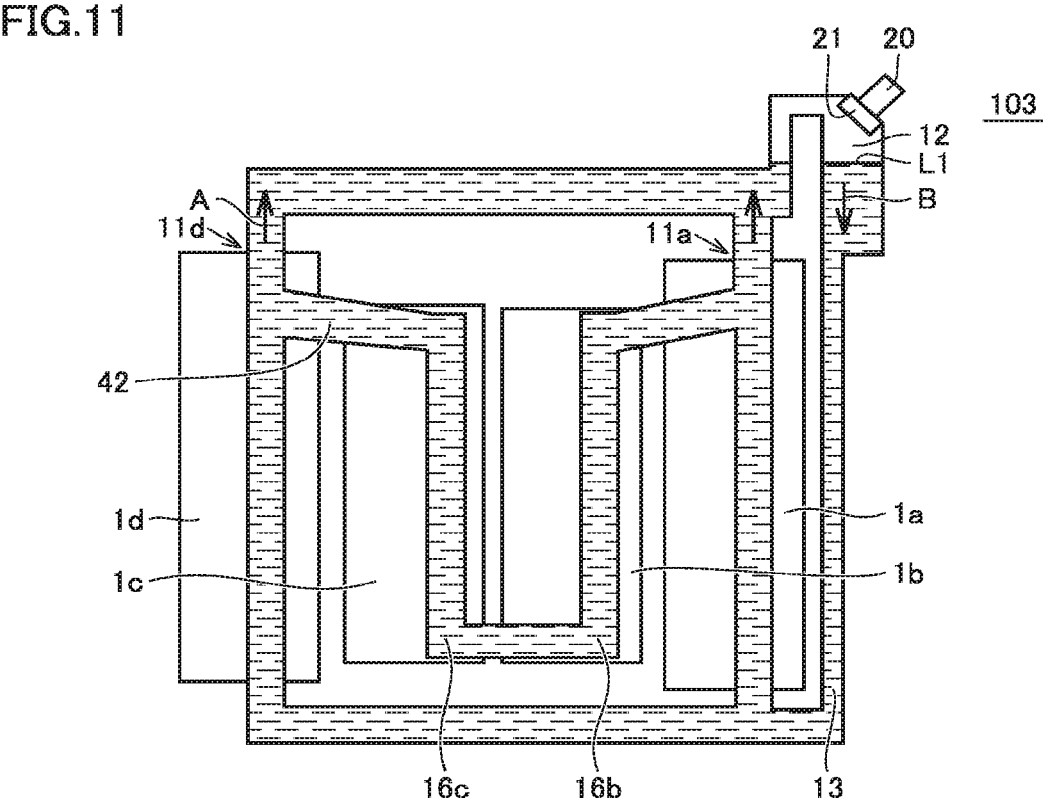
FIG. 11 is a diagram showing a liquid level of refrigerant in the refrigerant circulation circuit while a superconducting magnet apparatus according to a fourth embodiment is normally operating.
Figure 12:
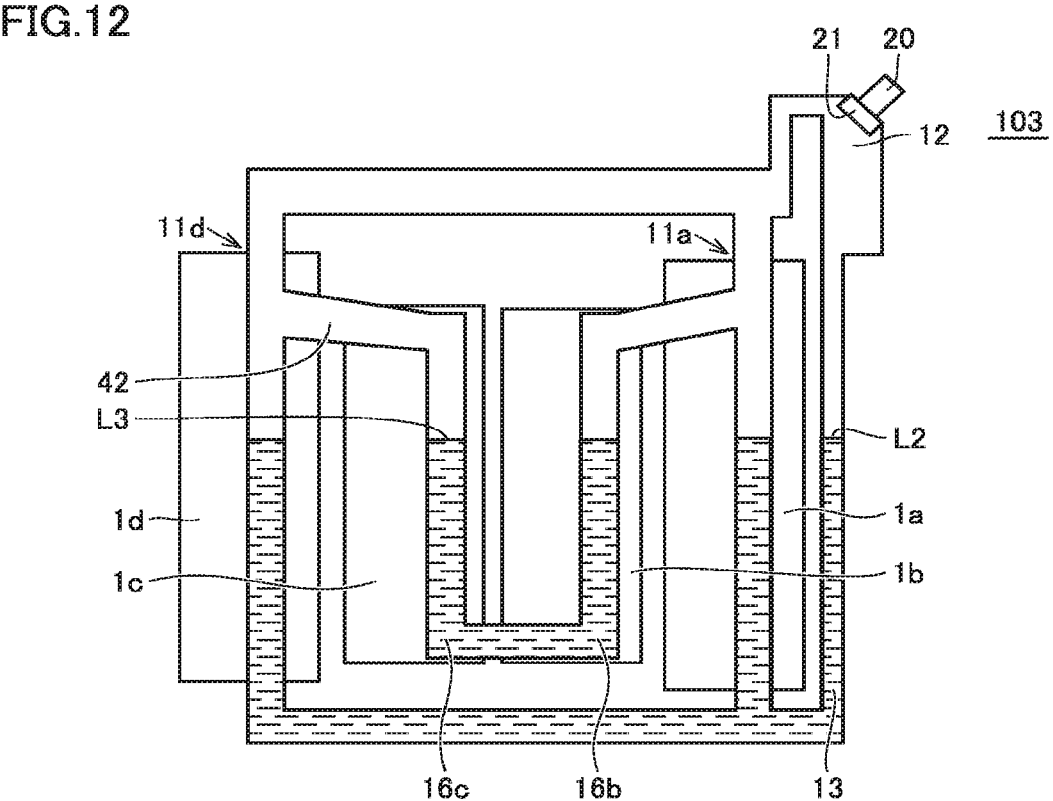
FIG. 12 is a diagram showing a liquid level of refrigerant in the refrigerant circulation circuit when a superconducting coil of the superconducting magnet apparatus according to the fourth embodiment is excited or demagnetized.

Though a superconducting magnet apparatus 103 according to a fourth embodiment is basically similar in construction to superconducting magnet apparatus 100 according to the first embodiment as shown in FIGS. 11 and 12, it is different in that refrigerant circulation circuit 10 further includes a communication pipe path 43 as a second communication pipe path that allows communication between first cooling pipe path 11a and fourth cooling pipe path 11d and second storage portion 16b and third storage portion 16c are made up by communication pipe path 43.

Communication pipe path 43 is branched from each of first cooling pipe path 11a and fourth cooling pipe path 11d. Communication pipe path 43 includes a central portion bent to protrude downward below respective opposing ends connected to first cooling pipe path 11a and fourth cooling pipe path 11d. Communication pipe path 43 is larger in inner diameter than first cooling pipe path 11a and fourth cooling pipe path 11d.

Specifically, communication pipe path 43 includes, for example a first portion 43a that is connected to first cooling pipe path 11a and extends along an axial direction, a second portion 43b that is connected to fourth cooling pipe path 11d and extends along the axial direction, and a third portion 43c that connects first portion 43a and second portion 43b to each other and is provided to protrude downward below first portion 43a and second portion 43b.

First portion 43a includes a portion in thermal contact with first superconducting coil 1a and a portion in thermal contact with second superconducting coil 1b. Second portion 43b includes a portion in thermal contact with fourth superconducting coil 1d and a portion in thermal contact with third superconducting coil 1c. Third portion 43c includes a portion in thermal contact with second superconducting coil 1b and a portion in thermal contact with third superconducting coil 1c.

Communication pipe path 43 is provided such that, when a liquid level of refrigerant in at least any one of first cooling pipe path 11a and fourth cooling pipe path 11d is lower than a portion of connection to communication pipe path 43, refrigerant remains therein. Namely, a portion of communication pipe path 43 in thermal contact with second superconducting coil 1b functions as second storage portion 16b. A portion of communication pipe path 43 in thermal contact with third superconducting coil 1c functions as third storage portion 16c.

Since superconducting magnet apparatus 103 is basically similar in construction to superconducting magnet apparatus 100, an effect similar to that of superconducting magnet apparatus 100 can be achieved.

Furthermore, in superconducting magnet apparatus 103, for example, when heat intrudes into first superconducting coil 1a in quantity larger than heat into other superconducting coils 1b to 1d and all of refrigerant in the liquid phase stored in first cooling pipe path 11a is evaporated, some of refrigerant in the liquid phase stored in communication pipe path 43 is supplied into first cooling pipe path 11a through communication pipe path 43. Refrigerant in the liquid phase is moved through communication pipe path 43 by gravity. Therefore, in superconducting magnet apparatus 103, occurrence of quench is prevented more effectively than in superconducting magnet apparatus 100 also when a quantity of heat intrusion is varied among the plurality of superconducting coils 1a to 1d.

As shown in FIG. 12, a larger amount of refrigerant in the liquid phase can be stored in communication pipe path 43 than in first cooling pipe path 11a and fourth cooling pipe path 11d. Therefore, for example, when second superconducting coil 1b and third superconducting coil 1c are more susceptible to heat intrusion from the outside than first superconducting coil 1a and fourth superconducting coil 1d as well, occurrence of quench in second superconducting coil 1b and third superconducting coil 1c can effectively be prevented.

Communication pipe path 43 is larger in inner diameter than first cooling pipe path 11a and fourth cooling pipe path 11d. Therefore, pressure loss of refrigerant that flows through communication pipe path 43 is less than in an example where communication pipe path 43 is equal in inner diameter to first cooling pipe path 11a and fourth cooling pipe path 11d from a point of view of reduction in amount of refrigerant. In particular, pressure loss of refrigerant caused by reversal of a direction of flow of refrigerant is significantly larger as the inner diameter of the pipe path is smaller. The direction of flow of refrigerant through communication pipe path 43 is reversed upward or downward depending on a state of operation of superconducting magnet apparatus 103. Therefore, in superconducting magnet apparatus 103 including communication pipe path 43 larger in diameter than first cooling pipe path 11a and fourth cooling pipe path 11d, increase in pressure loss due to reversal of the direction of flow of refrigerant is effectively suppressed.

Though superconducting magnet apparatus 103 shown in FIGS. 11 and 12 does not include second cooling pipe path 11b and third cooling pipe path 11c and first storage portion 16a and fourth storage portion 16d, limitation thereto is not intended. Superconducting magnet apparatus 103 according to the fourth embodiment may further include a plurality of cooling pipe paths 11a to 11d and a plurality of storage portions 16a to 16d similar in construction to those in any of superconducting magnet apparatuses 100 to 102 according to the first to third embodiments.

Fifth Embodiment

Figure 13:
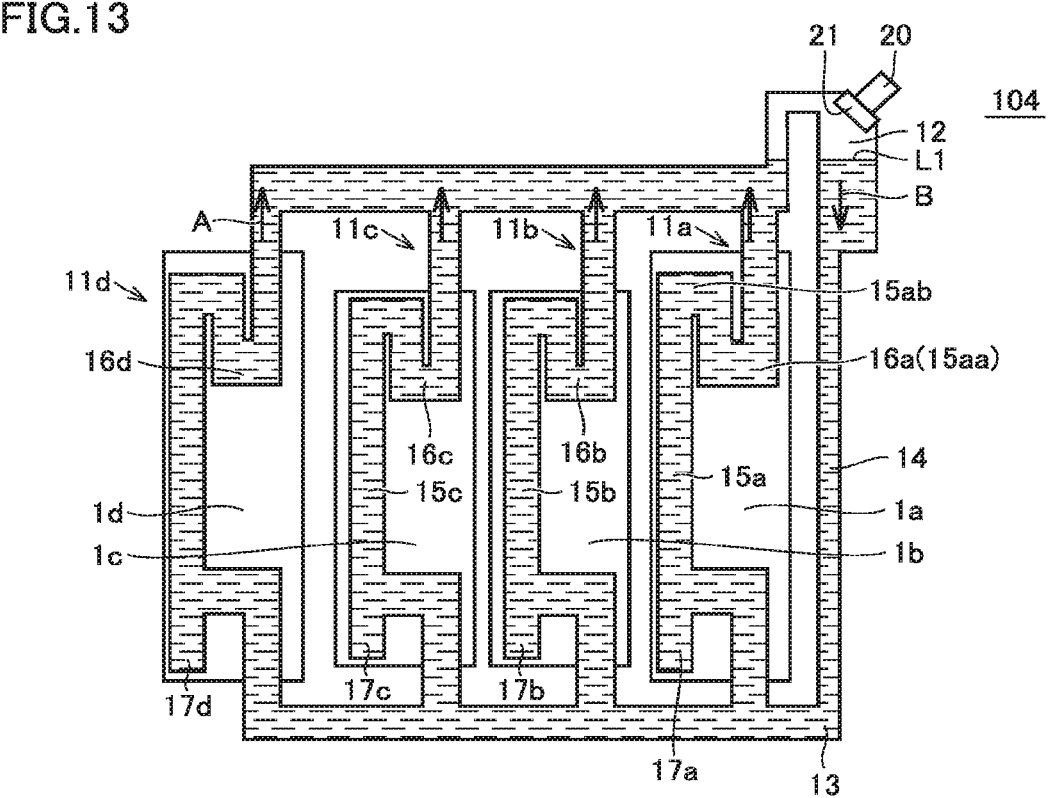
FIG. 13 is a diagram showing a liquid level of refrigerant in the refrigerant circulation circuit while a superconducting magnet apparatus according to a fifth embodiment is normally operating.
Figure 14:
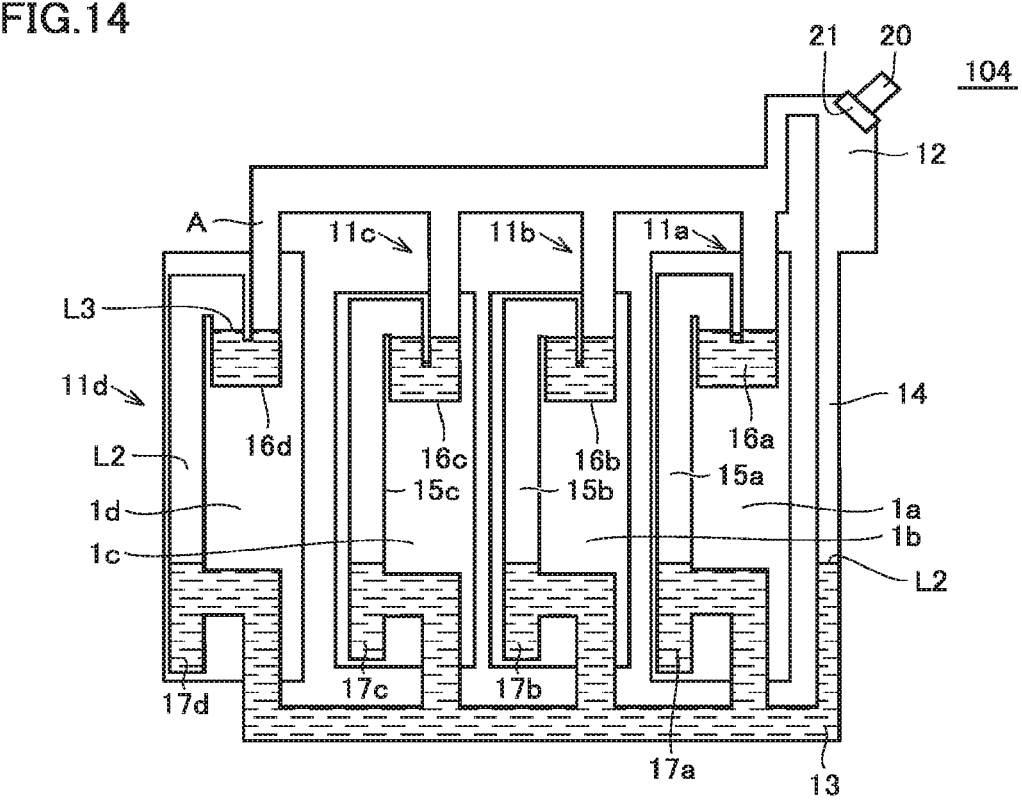
FIG. 14 is a diagram showing a liquid level of refrigerant in the refrigerant circulation circuit when a superconducting coil of the superconducting magnet apparatus according to the fifth embodiment is excited or demagnetized.

Though a superconducting magnet apparatus 104 according to a fifth embodiment is basically similar in construction to superconducting magnet apparatus 100 according to the first embodiment as shown in FIGS. 13 and 14, it is different in that storage portions 16a to 16d are made up by bent pipe portions formed by bending main pipe paths 15a to 15d, respectively.

First main pipe path 15a includes a first bent pipe portion 15aa bent to protrude downward and a second bent pipe portion 15ab connected between first bent pipe portion 15aa and the lower pipe path and bent to protrude upward above first bent pipe portion 15aa. In other words, a part of first main pipe path 15a is bent in an S shape or a Z shape to form first bent pipe portion 15aa and second bent pipe portion 15ab.

First bent pipe portion 15aa and second bent pipe portion 15ab are bent, for example, along the outer circumferential surface of first superconducting coil 1a. Namely, first bent pipe portion 15aa and second bent pipe portion 15ab are entirely in thermal contact with first superconducting coil 1a. First bent pipe portion 15aa and second bent pipe portion 15ab may be bent, for example, along the inner circumferential surface of first superconducting coil 1a or the outer circumferential surface of the frame.

First bent pipe portion 15aa is provided such that, when the liquid level of refrigerant in first main pipe path 15a becomes lower than second bent pipe portion 15ab, refrigerant remains therein. Namely, first bent pipe portion 15aa functions as first storage portion 16a.

Since superconducting magnet apparatus 104 is basically similar in construction to superconducting magnet apparatus 100, an effect similar to that of superconducting magnet apparatus 100 can be achieved.

Though superconducting magnet apparatus 104 shown in FIGS. 13 and 14 includes lower storage portions 17a to 17d similar in construction to those in superconducting magnet apparatus 100 according to the first embodiment, limitation thereto is not intended. Lower storage portions 17a to 17d may be formed by bent pipe portions formed by bending main pipe paths 15a to 15d, respectively, similarly to storage portions 16a to 16d.

Though embodiments of the present invention have been described as above, the embodiments described above can variously be modified. The scope of the present invention is not limited to the embodiments described above. The scope of the present invention is defined by the terms of the claims and is intended to include any modifications within the scope and meaning equivalent to the terms of the claims.

REFERENCE SIGNS LIST 1, 1a, 1b, 1d superconducting coil; 10 refrigerant circulation circuit; 11a first cooling pipe path; 11b second cooling pipe path; 11c third cooling pipe path; 11d fourth cooling pipe path; 12 upper pipe path; 13 lower pipe path; 14 connection pipe path; 15a first main pipe path; 15aa first bent pipe portion; 15ab second bent pipe portion; 15b second main pipe path; 15c third main pipe path; 15d fourth main pipe path; 16a first storage portion; 16b second storage portion; 16c third storage portion; 16d fourth storage portion; 17a, 17b, 17c, 17d lower storage portion; 18a, 18d, 19a protruding portion; 20 cooling portion; 21 low-temperature head; 31a first pipe portion; 32a second pipe portion; 33a third pipe portion; 34a fourth pipe portion; 35a fifth pipe portion; 40, 41, 42, 43 communication pipe path; 100, 101, 102 superconducting magnet apparatus

The invention claimed is:
1. A superconducting magnet apparatus comprising:
a superconducting coil centered around an axis extending in a direction intersecting with a vertical direction;
a refrigerant circulation circuit through which refrigerant circulates; and
a cooling portion that cools refrigerant,
the refrigerant circulation circuit including
a cooling pipe path in thermal contact with the superconducting coil,
an upper pipe path connected to the cooling pipe path and arranged above the cooling pipe path,
a lower pipe path connected to the cooling pipe path and arranged below the cooling pipe path, and
a connection pipe path that connects the upper pipe path and the lower pipe path to each other,
refrigerant sequentially circulating through the cooling pipe path, the upper pipe path, the connection pipe path, and the lower pipe path,
the cooling portion being provided to cool refrigerant in the upper pipe path,
the cooling pipe path including a storage portion where refrigerant is stored, and
a state being realized in which a liquid level of refrigerant is arranged within the storage portion, within a portion other than the storage portion in the cooling pipe path, and within the connection pipe path and the liquid level of refrigerant arranged within the other portion and the connection pipe path is arranged below the liquid level of refrigerant arranged within the storage portion.
2. A superconducting magnet apparatus comprising:
a superconducting coil centered around an axis extending in a direction intersecting with a vertical direction;
a refrigerant circulation circuit through which refrigerant circulates; and
a cooling portion that cools refrigerant,
the refrigerant circulation circuit including
a cooling pipe path in thermal contact with the superconducting coil,
an upper pipe path connected to the cooling pipe path and arranged above the cooling pipe path,
a lower pipe path connected to the cooling pipe path and arranged below the cooling pipe path, and
a connection pipe path that connects the upper pipe path and the lower pipe path to each other,
refrigerant sequentially circulating through the cooling pipe path, the upper pipe path, the connection pipe path, and the lower pipe path,
the cooling portion being provided to cool refrigerant in the upper pipe path,
the cooling pipe path including a storage portion where refrigerant is stored, wherein
the cooling pipe path further includes a main pipe path that connects the upper pipe path and the lower pipe path to each other, and
the storage portion is branched from the main pipe path.
3. The superconducting magnet apparatus according to claim 2, wherein
the superconducting coil includes a first superconducting coil and a second superconducting coil centered around the axis,
the cooling pipe path includes
a first cooling pipe path in thermal contact with the first superconducting coil and
a second cooling pipe path in thermal contact with the second superconducting coil and connected to the upper pipe path and the lower pipe path in parallel to the first cooling pipe path, the first cooling pipe path includes a first storage portion as the storage portion, the second cooling pipe path includes a second storage portion as the storage portion, the first storage portion is in thermal contact with the first superconducting coil, and the second storage portion is in thermal contact with the second superconducting coil.

4. The superconducting magnet apparatus according to claim 3, wherein the refrigerant circulation circuit further includes a first communication pipe path that allows communication between the first storage portion and the second storage portion.

5. The superconducting magnet apparatus according to claim 2, wherein the main pipe path includes a first pipe portion and a second pipe portion that extend along a circumferential direction around the axis and a third pipe portion that connects the first pipe portion and the second pipe portion to each other and extends along the axis, the second pipe portion extends downward from a position above a lower end of the first pipe portion, a portion of connection between the first pipe portion and the third pipe portion is arranged above the lower end of the first pipe portion, and the storage portion is made up by a portion in the first pipe portion that is located below the portion of connection.

6. The superconducting magnet apparatus according to claim 5, wherein a portion of connection between the second pipe portion and the third pipe portion is arranged below an upper end of the second pipe portion.

7. The superconducting magnet apparatus according to claim 2, wherein the cooling pipe path includes a plurality of cooling pipe paths connected to the upper pipe path and the lower pipe path in parallel to each other, the refrigerant circulation circuit further includes a second communication pipe path that allows communication between the plurality of cooling pipe paths, and the storage portion is made up by the second communication pipe path.

8. The superconducting magnet apparatus according to claim 7, wherein the superconducting coil includes a first superconducting coil and a second superconducting coil centered around the axis, the plurality of cooling pipe paths include a first cooling pipe path in thermal contact with the first superconducting coil, and the storage portion is in thermal contact with the second superconducting coil.

9. The superconducting magnet apparatus according to claim 1, wherein the cooling pipe path includes a main pipe path that connects the upper pipe path and the lower pipe path to each other, the main pipe path includes
a first bent pipe portion bent to protrude downward, and
a second bent pipe portion connected between the first bent pipe portion and the lower pipe path and bent to protrude upward above the first bent pipe portion, and the storage portion is made up by the first bent pipe portion.

10. The superconducting magnet apparatus according to claim 1, wherein the cooling pipe path farther includes, below the storage portion, a lower storage portion where refrigerant is stored.

11. The superconducting magnet apparatus according to claim 3, wherein the main pipe path includes a first pipe portion and a second pipe portion that extend along a circumferential direction around the axis and a third pipe portion that connects the first pipe portion and the second pipe portion to each other and extends along the axis, the second pipe portion extends downward from a position above a lower end of the first pipe portion, a portion of connection between the first pipe portion and the third pipe portion is arranged above the lower end of the first pipe portion, and the storage portion is made up by a portion in the first pipe portion that is located below the portion of connection.

12. The superconducting magnet apparatus according to claim 4, wherein the main pipe path includes a first pipe portion and a second pipe portion that extend along a circumferential direction around the axis and a third pipe portion that connects the first pipe portion and the second pipe portion to each other and extends along the axis, the second pipe portion extends downward from a position above a lower end of the first pipe portion, a portion of connection between the first pipe portion and the third pipe portion is arranged above the lower end of the first pipe portion, and the storage portion is made up by a portion in the first pipe portion that is located below the portion of connection.

13. The superconducting magnet apparatus according to claim 2, wherein the cooling pipe path further includes, below the storage portion, a lower storage portion where refrigerant is stored.

* * * * *